US00PP07861P

United States Patent [19]

Lopez

[11] Patent Number: Plant 7,861

[45] Date of Patent: May 5, 1992

[54] STRAWBERRY PLANT NAMED MILCIN

[75] Inventor: José M. A. Lopez, Tudela Navarra, Spain

[73] Assignee: Plantas de Navarra S.A., Navarra, Spain

[21] Appl. No.: 564,445

[22] Filed: Aug. 8, 1990

[51] Int. Cl.[5] ..... A01H 5/00

[52] U.S. Cl. ..... Plt./48

[58] Field of Search ..... Plt./48, 49

*Primary Examiner*—Howard J. Locker

*Attorney, Agent, or Firm*—Foley & Lardner

[57] ABSTRACT

A strawberry plant named Milcin particularly characterized by its generally globose shape, round leaves, large yellow-green flowers the petals of which are broader than they are long, relatively low stolon production, cylindrical fruit wherein the exterior surface is orange-red, and the flesh and core a lighter orange-red; calyx diameter similar to the diameter of the fruit; achenes are level with the surface, firm exterior, flesh and core, and its medium to strong juiciness and flavor.

2 Drawing Sheets

The present invention comprises a new and distinctive cultivar of strawberry plant referred to by the varietal name Milcin. The new cultivar was referred to by the number 85.116.03 during breeding and development. The new cultivar is a product of a planned breeding program. The basic objective of the breeding program was to create new strawberry cultivars particularly adaptable to growing conditions in Huelva, Spain with regard to fruit production, firmness, size, taste and color. The geographical location of Huelva, Spain, is 7° West and 37° North, near the Gulf of Cadiz.

The new cultivar was originated from a cross made in a controlled breeding program in Valtierra, Navarra, Spain. The male parent was the cultivar named Parker (U.S. Plant Pat. No. 5,263), and the female parent was the cultivar named Chandler (U.S. Plant Pat. No. 5,262).

Milcin was discovered and selected by me as a plant within the progeny of the stated cross in a controlled environment in Huelva, Spain. Asexual reproduction of the new variety by stolons, as performed by me at Soria, Spain (3° West and 41° North at 3,000 feet), has demonstrated that the combination of characteristics as herein disclosed for the new cultivar are firmly fixed and are retained through successive generations of asexual reproduction.

Milcin has not been observed under all possible environmental conditions. The phenotype may vary significantly with variations in environment, without, however, any variation in the genotype. The following observations, measurements and values describe the new cultivar as grown in Huelva, Spain under conditions which closely approximate those generally used in commercial practice.

The following traits have been repeatedly observed and are determined to be basic characteristics of Milcin, which in combination distinguish this strawberry plant as a new and distinct variety:

1. The terminal leaflet is approximately as long as it is broad, and the shape of the base is obtuse. The leaf color is medium to dark green, and the pose of hairs in the petiole is upward. Leaf cross-section is slightly concave.

2. The fruit is much longer than its maximum width, and is very large; shape is generally cylindrical although tapered.
3. Insertion of achenes is below level with the surface.
4. The diameter of the calyx is approximately the same as its fruit.
5. Plant vigor is strong, and shape is generally globose; fruit-bearing is not remontant.
6. Flowers are relatively large and generally above the foliage; diameter of calyx and corolla are approximately the same. Flowering time is later compared to the parents Parker and Chandler.
7. Exterior fruit color is orange-red, with the flesh and core being a lighter orange-red.
8. The flower petals are white in color and are much broader than long.
9. The number of stolons produced is relatively low compared to the stolen production of either plant.

The new cultivar is most similar to the male parent Parker, being similar thereto in the characteristics of leaf shape and color, position of inflorescence, calyx/corolla size ratio, and larger, generally cylindrical fruit. Milcin distinguishes from Parker by its relatively low stolon production, upward pose of petiole hairs, broader and shorter petals, calyx and fruit diameter being approximately the same, slightly concave leaf cross-section, stronger and more erect inflorescence, wider petals, red orange fruit color, harder fruit with a more elastic skin, and by its slightly later ripening.

The accompanying color photographic drawings show various features of typical specimen plants of the new cultivar.

Sheet 1 comprises a top photograph showing in top plan view a number of plants with fruit in various stages of maturity, and a bottom photograph showing whole fruit and longitudinal and transverse sections through the fruit to show the flesh.

Sheet 2 comprises a top photograph showing the upper and under surfaces of a typical mature leaf, and a bottom photograph showing in top plan view a number of flowers in bloom. The colors appearing in the photographs are as true as possible with color illustrations of this type.

In the following description, color references are made to The Royal Horticultural Society Colour Chart (R.H.S.), except where general colors of ordinary significance are referred to. Color values were taken at Huelva, Spain.

Parentage:

*Male parent.*—Parker.

*Female parent.*—Chandler.

Propagation: The number of runners produced is medium to low. Its ease of rooting is also average, less than Chandler and Parker in Soria, Spain. Its vigor in Soria is also average, less than Chandler and Parker.

PLANTS

A. Growth habit: Overall size is medium, similar in size to Parker.

B. Preferred planting: October in Huelva, Spain, with peak production occurring in March, April and May.

C. Leaves:

1. *Size.*—Medium, smaller diameter than Chandler.
2. *Shape.*—Terminal leaflet is as long as broad and base is obtuse; shape of teeth is obtuse.
3. *Color.*—Upper surface is light green, approximately 147A; under surface 147B.
4. *Growth habit.*—Globose.
5. *Other characteristics.*—Pose of petiole hairs upwards; leaf cross-section slightly concave.

INFLORESCENCE

A. Size and shape: Flowers are large and positioned above foliage. Similar to fruit diameter at ripening time (see chart below).

B. Peduncles: Erect.

C. Pedicels: Pedicels are erect and long; hairs upward.

D. Quantity: Very abundant.

E. Color: Petals are yellow-green, approximately 1C-D.

F. Anthers and pollen: Abundant and fertile.

G. Calyx: Inner and outer calyx approximately the same size, as is the size of calyx in relation to fruit diameter.

H. Number of petals: Ranges from 5 to 9.

J. Flowering period: With fresh plants in plantings carried out in October at Huelva, Spain, flowering takes place 80–90 days after planting.

FRUIT

A. Overall size and shape: The overall size of fruit is very large, larger than Chandler. Shape is almost cylindrical and longer than broad. The range of dimensions of the fruit of Milcin is as follows:

| | Length | Width |
|---|---|---|
| Maximum: | −7 cms. | 4 cms. |
| Minimum: | −2.5 cms. | 1.5 cms. |

B. Achenes: Achenes appear level with surface.

C. Juiciness: Medium.

D. Taste: Sweetness and acidity are medium.

E. Color: Orange-red exterior, approximately 44A; flesh and core are a somewhat lighter orange-red, approximately 44B-C.

F. Exterior Surface:

1. *Gloss.*—Very pronounced.
2. *Texture.*—Slightly uneven.
3. *Firmness.*—Strong.

G. Characteristics of flesh and core: Flesh is firm and same color as core.

H. Keeping qualities: Very good.

J. Fruit picking: Starts 30 to 40 days after flowering.

Disease resistance: Resistant to botrytis in wet weather. No special sensitivities to other diseases or parasites have been observed to date.

General observations: Spring bearing but with a slight tendency towards everbearing.

I claim:

1. A new and distinct cultivar of strawberry plant named Milcin, as illustrated and described.

* * * * *

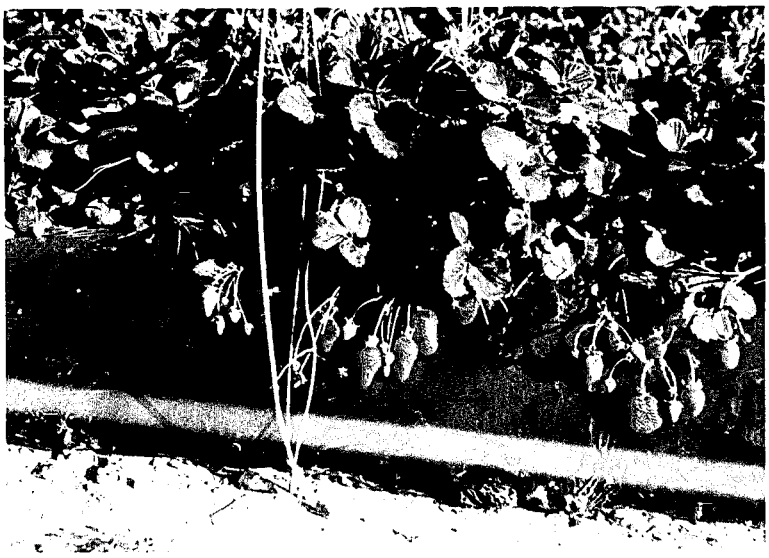
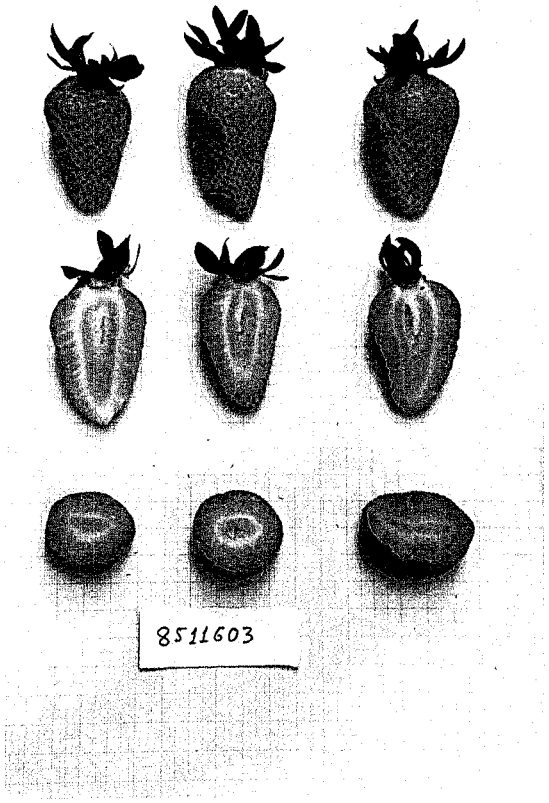
8511603

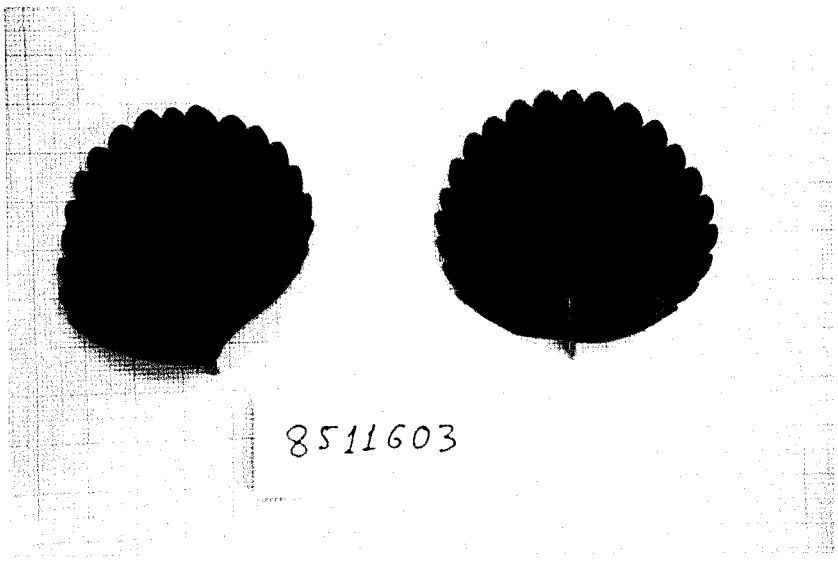
8511603
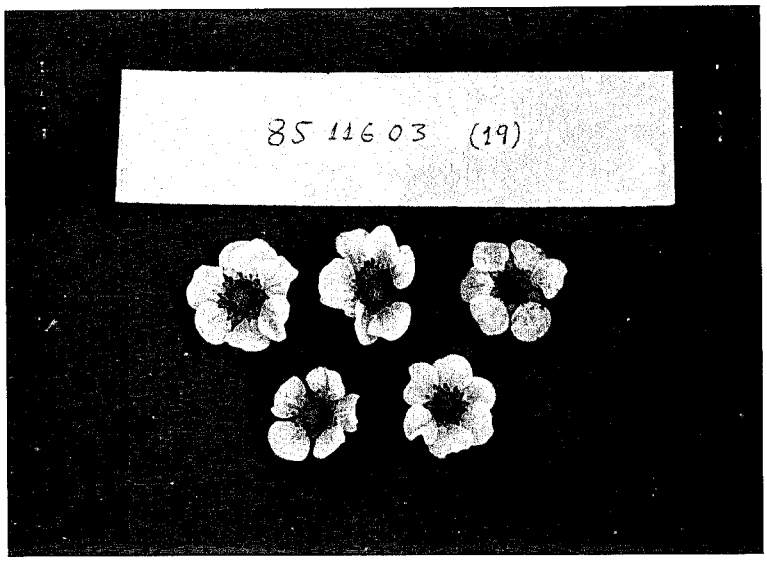
85 11603 (19)